United States Patent [19]

Nehring

[11] 4,022,209
[45] May 10, 1977

[54] RESILIENT SELF-CONTAINED FLUID EVACUATOR

[75] Inventor: John R. Nehring, Bergen, N.J.

[73] Assignee: International Paper Company, New York, N.Y.

[22] Filed: June 16, 1975

[21] Appl. No.: 587,142

Related U.S. Application Data

[63] Continuation-in-part of Ser. No. 417,124, Nov. 19, 1973, Pat. No. 3,889,677.

[52] U.S. Cl. .............................................. 128/278
[51] Int. Cl.² ...................................... A61M 1/00
[58] Field of Search .................... 128/276–278; 417/383, 386, 394, 472; 222/386.5; 141/7, 65, 66; 138/30

[56] References Cited

UNITED STATES PATENTS

| | | | |
|---|---|---|---|
| 2,074,223 | 3/1937 | Horiuchi | 128/231 |
| 3,032,037 | 5/1962 | Huber | 128/276 |
| 3,398,743 | 8/1968 | Shalit | 128/278 |
| 3,662,929 | 5/1972 | Sims | 222/386.5 |

*Primary Examiner*—Robert W. Michell
*Assistant Examiner*—Henry S. Layton
*Attorney, Agent, or Firm*—Finnegan, Henderson, Farabow & Garrett

[57] ABSTRACT

A self-contained wound evacuator is disclosed which provides a substantially constant negative gauge pressure and which includes a container and an air inflatable member within the container, the container and inflatable member having a combined configuration which avoids deformation of the inflatable member by the container in at least one direction of expansion of the inflatable member. Means are provided for inflating the inflatable member and controlling the deflation thereof.

18 Claims, 8 Drawing Figures

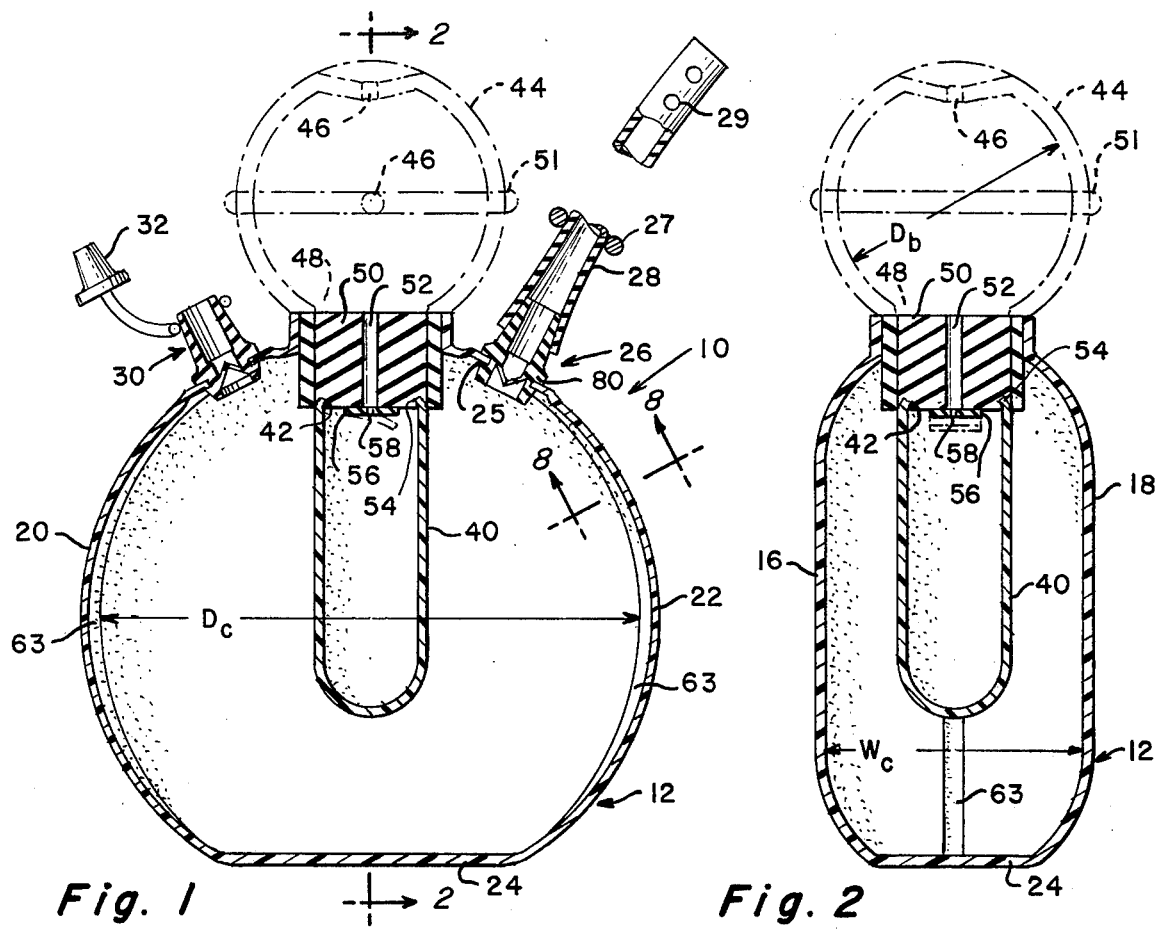
Fig. 1
Fig. 2
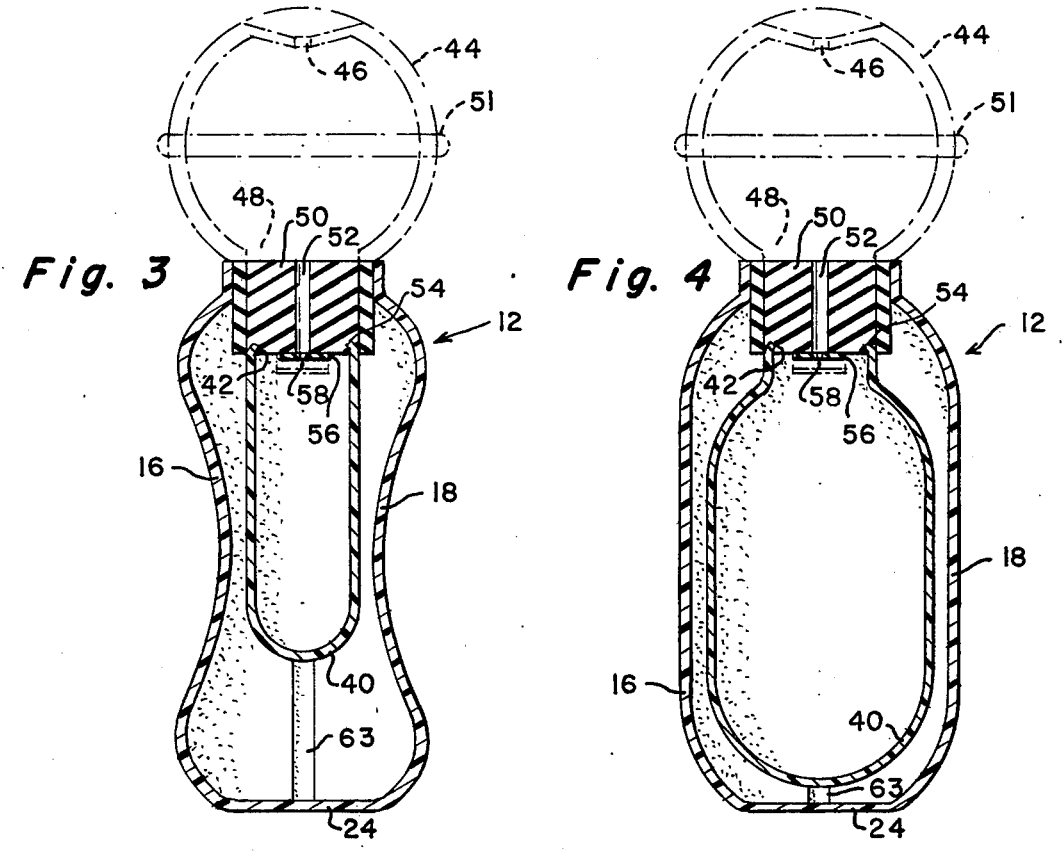
Fig. 3
Fig. 4

RESILIENT SELF-CONTAINED FLUID EVACUATOR

BACKGROUND

This application is a Continuation-in-Part of U.S. pat. application, Ser. No. 417,124, now U.S. Pat. No. 3,889,677, filed Nov. 19, 1973.

This invention relates to fluid evacuators and, more particularly, to such evacuators which are disposable, portable and self-contained.

The evacuation of fluids from the body of a patient is a common medical practice. For example, the removal of fluids from the vicinity of a wound has been found to aid faster and firmer healing and reduce the likelihood of infection, fever and patient discomfort. Fluid evacuation usually is accomplished through gravity drainage, pressure dressings, compression bandages or by negative pressure, the latter being preferred. Conventional continuous closed wound suction devices include power driven vacuum pumps, central suction systems or evacuated bottles. With the exception of the evacuated bottle, each of these systems has many disadvantages because of their cost, noise and restriction of patient mobility resulting in the retardation of post operative exercises, ambulation and rehabilitation.

Other suction wound drainage systems were developed to overcome these disadvantages. Examples of more recent commonly used wound evacuators are shown in U.S. Pat. Nos. 3,115,138 and 3,376,868. In both of these devices the evacuator comprises an evacuation chamber formed with resilient side walls which, after manual compression and release, tend to return to their original extended position. In so returning they provide a reduced pressure on the interior of the container which, when attached to the patient by means of a tube, effects evacuation of the wound. A potential hazard with such a device is the possibility of accidental compression in the container when the device is attached to the patient could result in the injection of air or previously removed fluids into the patient. Another disadvantage with devices of this type is their wide variation of negative pressure over the specified filling range of the devices. When empty and fully compressed these devices often provide a vacuum higher than necessary which might cause lesions if tissue is sucked into or against the drainage tube. On the other hand, as the container becomes filled with fluid the vacuum is reduced often to a level where the vacuum is relatively ineffective and clots or other debris may clog the drainage tube. Wound evacuators presently commercially available have total pressure variations of about 130% or more.

Accordingly, it is an objective of this invention to provide an inexpensive, reliable, disposable, portable, self-contained vacuum drainage device which evacuates fluids from wounds at relatively constant pressure throughout the entire operating range of the device.

It is another objective of this invention to provide an improved self-contained wound evacuator which when accidentally pressurized will not cause accidental injection of air or fluids into a patient.

Additional objectives and advantages of the invention will be set forth in part in the description which follows, and in part will be obvious from the description, or may be learned by practice of the invention. The objectives and advantages of the invention may be realized and attained by means of the instrumentalities and combinations particularly pointed out in the appended claims.

SUMMARY OF THE INVENTION

To achieve the foregoing objectives and in accordance with the purpose of the invention as embodied and broadly described herein, the self-contained fluid evacuator of this invention comprises a container having at least one resilient wall capable of being deformed. The container has sufficient resilience to return to an undeformed state upon the release of pressure deforming the container. A resilient inflatable member is placed within the container with the interior surface of the container and the exterior surface of the inflatable member defining a fluid receiving chamber. The inflatable member has an opening therethrough connecting the interior of the member with the exterior of the container. The opening includes means for restricting flow through the opening from the inflatable member. An inlet and an outlet in the container provide flow communication with the fluid receiving chamber. The outlet includes a one-way valve permitting flow into the fluid receiving chamber. External deformation of the container and its subsequent resilient recovery to its undeformed states lowers the pressure within the fluid receiving chamber. This low pressure within the chamber inflates the inflatable member by allowing air flow through the opening into the inflatable member. Subsequent deflation of the inflatable member produces a substantially constant negative pressure in the chamber thereby drawing fluid through the inlet. Preferably, the evacuator would include an inlet valve capable of closing the inlet to prevent the flow of material from the fluid receiving chamber through the inlet.

The invention consists in the novel parts, constructions, arrangements, combinations and improvements shown and described in the accompanying drawings which are incorporated in and constitute a part of the specifications illustrate several embodiments of the invention and together with the description serve to explain the principles of the invention.

BRIEF DESCRIPTION OF THE DRAWINGS

Of the drawings:

FIG. 1 is a cross-sectional view of one embodiment of the invention.

FIG. 2 is a cross-sectional view of the embodiment of FIG. 1 along lines 2—2.

FIG. 3 is a cross-sectional view similar to that of FIG. 2 showing the deformed resilient side-walls.

FIG. 4 is a cross-sectional view similar to that of FIGS. 2 and 3 showing the inflation of the inflatable member as a result of the deformation of the side-walls.

DESCRIPTION OF THE PREFERRED EMBODIMENTS

Figure 5:
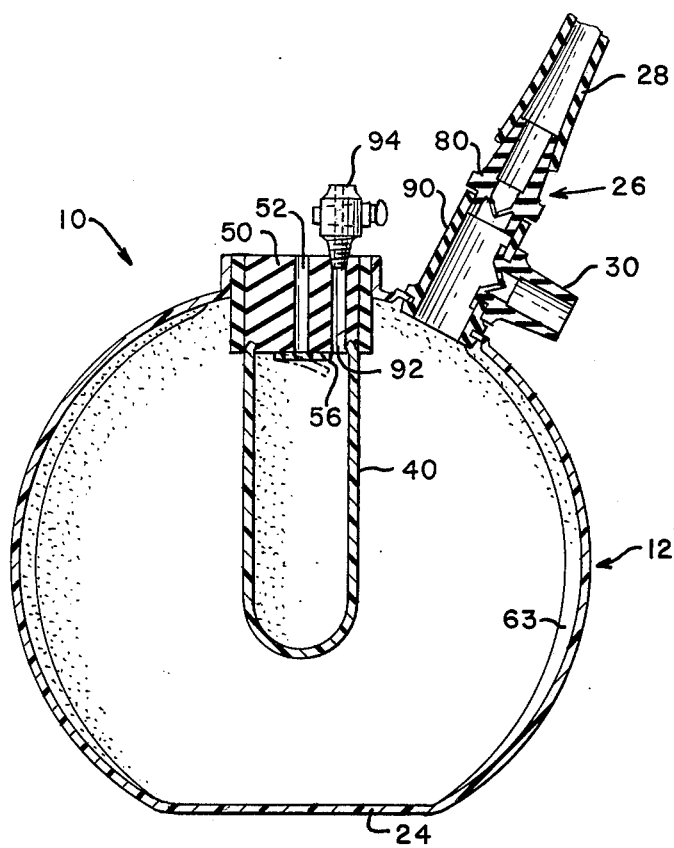
FIG. 5 is a cross-sectional view of another embodiment of the invention.

Throughout the specification and claims, terms of orientation, such as front, back, up and down are employed with respect to the orientation shown in the drawings in order to simplify description of the invention and are not intended to limit the location or direction of the elements with respect to which these terms are used.

In accordance with the invention, the wound evacuator includes a housing and a first port serving as a fluid inlet port communicating with the interior of the housing. The first port is adapted to receive a tube designed to be placed internally within a patient adjacent to a wound in order to remove fluids from the vicinity of the wound. As here embodied, a self-contained wound evacuator 10 is formed with a container 12 having opposed first and second side walls 16, 18 (hereinafter called front and back walls), opposed third and fourth side walls 20, 22 adjacent to the front and back walls 16, 18 and a bottom wall 24. The container 12 is relatively resilient which means that it will deform substantially when it is subjected to substantial external pressure. The container 12 is provided with at least one opening, such as opening 25, extending through and communicating with the interior of the container 12. The opening 25 is adapted to receive inlet and outlet means with the inlet means adapted to receive flexible tubing 28 which is to be inserted into a patient adjacent to the wound being treated. The tubing 28 is conventional wound tubing which is non-toxic, non-pyrogenic, inert, non-porous and non-degradable when used in its intended environment and which has a plurality of openings 29 at its distal end.

While a single opening 25 is sufficient for operation of the self-contained wound evacuator 10 as described below, it is preferred that a second opening in the container be provided for an outlet 30. The outlet 30 permits expulsion of air contained within the container 12 and permits removal of fluid which is received within the container 12 during utilization of the wound evacuator 10. The outlet 30 should include a one-way valve preventing flow into the container 12. A suitable closure or cap 32 may be provided to permit selective opening and closing of the outlet 30.

In accordance with the invention an air inflatable member is mounted within the container 12 and means for inflating and deflating the inflatable member are provided. As here embodied, the inflatable member is a resilient bladder 40 having an opening at one end 42 thereof. The means for inflating the bladder 40 preferably is a manually operated pump, such as a hand-operated bulbous resilient member having a resiliency at least only slightly greater than the resiliency of the bladder 40. Such a resilient member is a rubber bulb 44 having an air inlet 46 and an open neck 48. The open end 42 of the bladder 40 is mounted in the neck 48 of the bulb 44 so that air expelled through the bulb neck 48 is forced to enter the bladder 40. While the bladder can be mounted directly on the walls of the bulb neck 48, the embodiment illustrated in FIGS. 1–5 employs a plug 50 which is force-fitted within the neck 48, the plug 50 having an air passageway 52 axially therethrough. The plug 50 is provided with an annular recess 54 to receive the open end 42 of the bladder, the open end of the bladder being trapped between the exterior of the plug 50 and the interior of the bulb neck 48 to fixedly hold the bladder in place. The bulb 44 serves as the means to inflate the bladder 40 while the resiliency of the bladder serves as the means for deflating the bladder.

While the bulb air inlet 46 is shown at the top of the bulb 44, it could be located at any other position. For example, with a container 12 as shown, locating the air inlet on the side has been found particularly convenient because it is easier to block the air inlet 46 with a finger or the heel of a hand. Furthermore, in order to ensure quick opening of the inlet 46 on release of the bulb so that the bulb quickly refills with air entering through the inlet 46 rather than being withdrawn from the bladder 40, an irregular surface, such as a bead 51 is provided through which the inlet is formed. The bead 51 prevents the finger or hand from sealing the inlet during return of bulb to normal unsqueezed condition.

Further in accordance with the invention, valve means for provided which are responsive to the difference in pressure between the bulb 44 and the bladder 40 so that when the pressure in the bulb exceeds the pressure in the bladder, the valve means permit free flow of air from the bulb to the bladder. However, when the pressure in the bladder 40 exceeds the pressure in the bulb 44, the valve means restrict the flow rate from the bladder to a predetermined minimal quantity.

In order to control the rate of deflation of the bladder 40, a slow leak check valve, such as a flapper valve 56 having a small diameter bleed vent 58 therethrough, is mounted on the bladder side of the plug 50. When the bulb 44 is squeezed, the flapper valve 56 permits air to be expelled freely from the bulb into the bladder 40 since the pressure differential across the flapper valve 56 during such an operation forces the flapper away from the plug 50 thereby permitting air to flow easily into the bladder 40. However, when the bladder is partially or totally inflated and the bulb 44 is returning from its squeezed or collapsed position to its normal or expanded position, the pressure within the bladder is higher than the pressure within the bulb and the flapper valve is forced against the plug 50 thereby obturating the air passageway 52 except for the vent 58 and preventing most of the air from leaving the bladder 40. After the bladder is fully inflated and the wound tubing 28 is inserted in a patient for evacuation, the small bleed vent 58 permits air to be expelled from the bladder 40 through the passageway 52.

While the embodiment of FIGS. 1 through 4 can be utilized with the squeeze bulb 44 to inflate the bladder 40, the improvement of the present invention allows the bladder 40 to be inflated either with the squeeze bulb 44 or the deformation of the resilient container 12. FIGS. 2 through 4 shows the sequence of filling the bladder 40 by deformation of the resilient container. FIG. 2 depicts the apparatus in an undeformed state with the shape of the bladder 40 assuming its natural shape. FIG. 3 depicts the container 12 in the deformed condition where sidewalls 16 and 18 are deformed thereby reducing the volume of the container. The valve 56 prevents significant flow of air from the bladder 40. FIG. 4 shows the configuration of the bladder 40 subsequent to the resilient recovery of the container sidewalls 16 and 18.

The exterior of the bladder 40 and the interior of the container 12 form the fluid receiving chamber. The expulsion of air from the chamber and subsequent resilient recovery of the container creates a differential pressure across the bladder 40 that draws air through the opening 52 to inflate the bladder 40. A negative pressure is generated in the container 12 when the bladder 40 is allowed to deflate, as for example, through the bleed hole 58. It should be noted that while the shape of the container 12 depicted herein is preferred, other configurations of containers would be operable with the present invention. Generally the container must have at least one resilient wall capable of being deformed and the container must have sufficient resilience to return to the undeformed state upon the release of the pressure deforming the container.

To utilize the self-contained wound evacuator 10 of this invention the distal end of the wound tubing 28 is inserted in the patient before the proximal end is connected to the inlet port 26. Alternatively, the wound tubing 28 can be connected to the container 12 and closed by a conventional pinch clamp 27. The closure 32 is removed from the outlet port 30 and the bladder 40 is inflated by alternately squeezing and releasing the bulb 44 or the resilient container 12. When squeezing the bulb 44 the user covers the air inlet 46 to prevent air from being expelled through the inlet, thereby requiring that all air expelled from the bulb 44 passes through the air passageway 52 into the bladder 40. When the bulb is released air enters the bulb through the inlet 46. The flapper valve 56 prevents a substantial amount of air from flowing from the bladder 40 back into the bulb 44. Continued pumping of the bulb inflates the bladder 40 which forces the air within the container 12 out through the outlet port 30 until such time as the inflated bladder substantially fills the container 12. At that time, the proximal end of the wound tubing 28 is connected to the inlet port 26 (or the pinch clamp 27 is opened) and the closure 32 is placed in the outlet port 30 thereby closing the port. As the bladder deflates, the air in the bladder passes outwardly through the bleed vent 58, the air passageway 52 and the bulb air inlet 46. Deflation of the bladder 40 produces a negative pressure at the port 26 which causes fluids in the vicinity of the openings 29 at the distal end of the wound tubing 28 to pass through the tubing into the container 12.

After the container 12 is filled with body fluid, the container is emptied, either by attaching the port 30 to the low pressure side of a pump and pumping the fluid out or by closing the pinch clamp on the inlet and inflating the bladder 40. As the bladder inflates, it forces the body fluid out of the container and, when empty the bladder is fully inflated and the wound evacuator 10 is ready for reuse.

Figure 6:
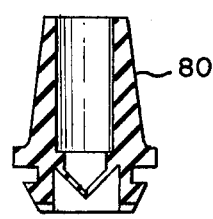
FIG. 6 is a cross-sectional view of the preferred check valve utilized with the present invention.
Figure 7:
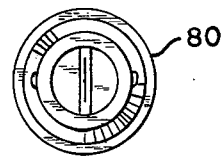
FIG. 7 is an end view of the check valve depicted in FIG. 6.

As here embodied the container 12 has a separate inlet and outlet, 26 and 30 respectively. The inlet depicted in FIGS. 1 and 5 comprises a one-way valve, a preferred embodiment of which is depicted in detail in FIGS. 6 and 7. In the embodiment depicted the inlet 26 only allows flow into the container 12. The inlet 26 may also include inlet valve means, an example of which is the pinch clamp 27 previously disclosed. The inlet valve means would be used to close the inlet 26 during inflation of the container 12 by the deformation of the resilient container walls.

The inlet 26 and the outlet 30 may also be located in a common conduit that comprises the sole means of flow communication to the interior of the container 12. As depicted in FIG. 5 the common conduit 90 is Y-shaped with the inlet 26 and outlet 30 located in separate branches of the Y. In such a configuration the inlet 26 preferably includes a one-way valve preventing flow through the inlet 26 from the container 12. In that manner the container can be emptied without the possibility of collected material passing from the container into the tube 28.

FIG. 5 depicts a preferred embodiment of the invention where the means of inflating the bladder 40 is solely the deformation of the resilient container 12. In this embodiment the opening 52 is in flow communication with the atmosphere. The flow restricting means in this embodiment is a one-way valve 56 comprising a flap valve without a bleed passage therethrough. Means are provided to bypass the one-way valve to vent the interior of the bladder 40 to the atmosphere thereby deflating the bladder 40 and generating the negative pressure within the container 40.

As here embodied and depicted in FIG. 5 the venting means comprises passage 92 with the associated manually controlled vent valve here embodied as petcock valve 94. The venting means depicted are not the only means of venting the bladder and one skilled in the art can devise venting means appropriate venting means with no further specific teaching. For example, external means of forcing flap valve 56 off its seat could be utilized as the venting means.

To utilize this embodiment of FIG. 5 the inlet 26 or the tube 28 are closed to prevent airflow into the container 12. The container is deformed lowering the volume within it through said forcing the contents of the container out the outlet 30. Upon resilient recovery of the container 12 the pressure within the container is lowered thereby drawing air into the bladder 40 past the one-way valve 56 through the opening 52. Multiple deformations of the container 12 may be necessary to completely fill the bladder 40 within the container 12. Once the bladder is sufficiently inflated the device may be utilized by opening the inlet 26 and the valve 94 whereby the bladder 40 deflates through opening 92 creating a negative pressure in the container 12. It is preferred that the flow of air through opening 92 be restrained thereby limiting the rate of negative pressure buildup within the container 12. The most convenient means of controlling the flow through opening 92 is by means of its size. One skilled in the art may preselect the rate of negative pressure buildup by preselecting the size of the opening 92.

In order to provide substantially constant negative pressure at the inlet port 26 throughout the entire operating range of the wound evacuator 10, and to utilize substantially the entire volume of the container, the container 12 and the bladder 40 should have a combined actual and effective configuration so that the container does not physically interfere with or distort the inflation of the bladder 40 in at least one direction of inflation. The terms "constant pressure" and "substantially constant pressure" as used throughout this specification and in the claims are intended for use in a relative sense and do not imply absolute constant or unchanging pressure. For example a total pressure variation of up to about 20–30% throughout about 90% of the deflation range is acceptable.

A low profile container 12 (relatively narrow from front 16 to back 18) is preferred because it can be more comfortably and conveniently worn by a patient or attached to a support, such as a bed or chair. These advantages can be obtained if the front and back walls 16, 18 are substantially flat and relatively closely spaced apart. Substantially flat front and back walls are walls which either are truly flat or which have a radius of curvature much greater than the radius of the bladder 40 when the bladder contacts the front and back walls 16, 18. When a substantial vacuum is to be induced in the container 12, it may be preferred to form the front and back walls 16, 18, with a shallow outward curvature (large radius of curvature) to provide structural strength without adversely affecting the the low profile of the container.

It also is desirable to be able to stand the container 12 vertically on a flat surface and, therefore, the bottom wall 24 of the container preferably should be flat.

It has been found that satisfactorily constant pressure can be obtained with a cylindrical bladder when the bladder is inflated in a low profile container ("flat" front and back walls) if the side walls 20, 22 adjacent to the "flat" front and back walls 16, 18 actually or effectively conform to the shape of the inflated bladder 40.

Figure 8:
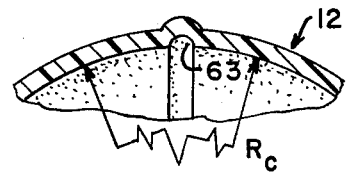
FIG. 8 is a cross-section along lines 8—8 in FIG. 1.

In order to actually conform the side walls 20, 22 to the bladder shape, the side walls 20, 22 are formed with a transverse outward curvature (from front wall to back wall) as can be seen in FIG. 8. Preferably, the radius of transverse curvature is $W_c/2$ where $W_c$ is the distance between the front and back walls 16, 18. It also is desirable to avoid corners at the top and bottom of the side walls and, therefore, rounded upper and lower ends are formed or, alternatively, the side walls 20, 22 can be formed with a longitudinal curvature from top to bottom as can be seen in FIGS. 2 and 5.

While satisfactory results can be obtained over a relatively wide range of front-to-back wall spacing, more consistently reliable results and more useful filling volume for a given container size while maintaining relatively constant pressure can be obtained if the front and back walls 16, 18 are spaced apart a distance greater than twice the diameter of the uninflated bladder ($W_c > 2D_f$).

In accordance with this invention, instead of actually conforming the sidewalls 20, 22 to the inflated bladder shape, the side walls 20, 22 can be made to "effectively" conform to the bladder shape by controlling the pressure within the container. More specifically, as the bladder 40 is inflated, the air inside the container 12 is expelled through the outlet port 30 until, after the bladder contacts the side walls 20, 22 and continues to inflate, it reaches a position within the container wherein the bladder is about to be forced into a shape which is different from what it would be if the side walls 20, 22 were nonexistent. At that time, the outlet port is occluded to prevent further expulsion of air from the container 12. Any further pressurization of the bladder 40 by further deformation of the resilient container 12 or by pumping the bulb 44 results in a concomitant increase in pressure inside the container since the air cannot escape. Upon deflation of the bladder 40 the pressure in the container rapidly drops to atmospheric pressure by virtue of the air in the bladder 40 escaping through the check valve bleed port 58 and bulb air inlet 46 to the atmosphere or the opening 92 in the embodiment depicted in FIG. 5. This concept of pressure equalization in the container and bladder when the bladder is about to be deformed into a shape which adversely affects a constant pressure curve is referred to throughout the specification and claims as "effective" conformation of the container shape with the bladder shape.

With respect to a container which actually conforms to the bladder shape and which has a satisfactory low profile, substantially constant negative pressure during deflation of a bladder has been obtained with a container and latex cylindrical bladder having the shapes generally shown in FIGS. 1, 5, and 8 and having the following dimension ratios.

$D_f$ = diameter of bladder;
$L_f$ = length of bladder = 3.0 – 4.0 $D_f$
$W_c$ = width of container = 2.5 $D_f$
$R_c$ = radius of transverse curvature of side walls = $W_c/2$
$D_c$ = length of container = 1.8$L_f$
$P_c$ = container interior perimeter <22$D_f$ The bladder thickness ($F_t$) together with the characteristics of the bladder material (actually, the modulus of elasticity) determines the vacuum level produced within the container. For a latex bladder, a bladder thickness of 0.01$D_f$ has been found to produce a constant negative pressure in the above described container of approximately 30 inches of water. The container perimeter/bladder diameter ratio is calculated to provide not greater than a seven fold increase in bladder perimeter which has been found to be within a safe stress range for a latex bladder. For a convenient and comfortable evacuator profile, the bulb diameter ($D_b$) should be approximately equal to the width of the container ($D_b = W_c$).

These ratios provide a self-contained wound evacuator having satisfactory performance by providing relatively constant pressure in a desired pressure range (−29 to −35 inches of water) and a safe stress for a bladder made of natural latex. The bladder can also be formed from any synthetic elastomer, such as polyurethane.

The container 12 can be formed of any suitable material such as a moldable plastic, for example, polyvinylchloride. The shape of the container lends itself to being blow molded; however, it could be formed other ways, such as by injection molding. As previously disclosed the container 12 must be constructed in a manner that it will regain its undeformed shape when the external deforming pressure is removed.

Further in accordance with the invention, it is desirable to provide means for preventing accidental sealing of a portion of the container from the outlet 30, especially during evacuation of fluids within the container 12 which were removed from the patient. One means for avoiding this blockage is to provide a recess 63 in the interior surface of the container walls, particularly in the area leading to and adjacent to the outlet port 30. Such a recess 63 assures the existence of a fluid flow passageway from the interior of the container 12 to the outlet 30. Also, the interior surface of the container walls can be roughened, such as by injection molding the container, to accomplish the same results.

A means for minimizing bladder to stress is to provide a surface coating on the interior surface of the container 12, or on the exterior surface of the bladder 40, which will lessen adherence of the bladder to the interior of the container. For example, it has been found that chlorinating the surface of a latex bladder or coating the interior surface of a container with a conventional commerically available medical silicone fluid successfully lessens adherence of the bladder to the container walls. Reduction of the adherence of the bladder 40 to the container walls also is of substantial assistance in maintaining the negative pressure substantially constant.

In order to operate the resilient bulb 44 illustrated in FIGS. 1 through 4, it is necessary for the user to place his finger over the air inlet 46 while squeezing the bulb 44 to prevent air from escaping through the air inlet 46 and thereby forcing that air into the inflatable bladder 40. The combined operation of simultaneously closing the air inlet 46 and squeezing the bulb 44 is a safety feature to prevent accidental injection of air or previously removed fluid into the patient since it is unlikely that both steps will accidentally be performed.

To further protect against accidental ejection of air or liquid through the port 26, a check valve, such as a valve 80, can be mounted within the inlet 26 for closing the inlet 26 upon pressurization of the container, such as if the bulb 44 is accidentally squeezed or the resilient container 12 deformed. Of course, the check valve 80 does not interfere with the flow of fluid into the container 12 through the wound tubing 28. Furthermore, the inlet 26 can be formed such that the bladder 40 occludes the port 26 when the bladder is inflated to its intended volume to further ensure against leakage through the inlet 26 to the patient.

It is also contemplated that a bulb can be used which has the same capacity as a fully inflated bladder. In other words, a single compression of the bulb would be sufficient to complete the inflation of the bladder. With a bulb of this size there is no requirement for an air inlet 46 and a closed system can be formed wherein air from the bulb fills the bladder and, when the bladder deflates, the air returns to the bulb for subsequent use. In such a closed system, a supple bulb, less resilient than the bladder, is used.

SUMMARY

It can be seen that the fluid evacuator of this invention is completely self-contained, portable and totally reliable. It is also easy and inexpensive to manufacture and, therefore, disposable. Of considerable significance are the safety features which prevent the fluid evacuator from being accidentally pressurized in a manner which will inject air or previously removed fluids back to the patient. Furthermore, the negative pressure formed at the inlet port which causes the forced removal of fluid from the patient is substantially constant thereby, (a) avoiding potential injury to the patient which could occur if the negative pressure is too high and (b) ensuring efficient operation of the evacuator throughout the entire operational range of the wound evacuator.

What is claimed is:

1. A self-contained fluid evacuator comprising:
  a. a container having at least one resilient wall capable of being deformed inwardly by applying an external pressure thereon, said resilient wall having sufficient resilience to return to an undeformed state upon release of said external pressure;
  b. a resilient inflatable member within said container resiliently expandable between a natural state and a resiliently enlarged deformed state, the interior surface of said container and the exterior surface of said inflatable member defining a fluid receiving chamber therebetween, said inflatable member having an opening therethrough connecting the interior of said inflatable member with the exterior of said container, said opening including means for restricting flow through said opening from said inflatable member;
  c. an inlet in said container in flow communication with said chamber, said inlet being adapted to receive said fluid; and
  d. an outlet in said container in flow communication with said chamber, said outlet including a one-way valve preventing flow into said chamber;
  e. said one container wall being deformable inwardly to flow air outwardly of said chamber through said container outlet to reduce the volume of said chamber, said inflatable member being expandable from said natural state to its resiliently enlarged deformed state by flow of air through said opening into said member in response to return of said one container wall to its undeformed state and the reduced pressure generated thereby in said chamber whereupon return of the inflatable member to its natural state under force of its natural resilient bias flows air outwardly of said member through said restricted opening and produces a substantially constant negative pressure in said chamber for drawing fluid through said inlet into said chamber.

2. The fluid evacuator of claim 1 wherein said inlet includes inlet valve means for cloasing said inlet during inflation of said inflatable resilient member.

3. The fluid evacuator of claim 2 wherein said inlet valve means is a one-way valve only allowing flow into said chamber.

4. The fluid evacuator of claim 1 where said resilient inflatable member is a substantially cylindrical bladder.

5. The fluid evacuator of claim 1 wherein said evacuator further includes means for closing said inlet, a flexible tube mounted on said inlet and valve means for closing said tube.

6. A self-contained fluid evacuator comprising:
  a. a container having at least one resilient wall capable of being deformed inwardly by applying an external pressure thereon, said resilient wall having sufficient resilience to return to an undeformed state upon release of said external pressure;
  b. a resilient inflatable member within said container, the interior surface of said container and the exterior surface of said inflatable member defining a fluid-receiving chamber therebetween, said inflatable member having an opening therethrough connecting the interior of said inflatable member with the exterior of said container, said opening including means for restricting flow through said opening from said inflatable member;
  c. an inlet in said container in flow communication with said chamber, said inlet being adapted to receive said fluid;
  d. an outlet in said container in flow communication with said chamber, said outlet including a one-way valve preventing flow into said chamber; and
  e. a resilient squeeze bulb in flow communication with said opening and said flow restricting means comprising a one-way valve, said valve including a bleed passage therethrough, said bleed passage having a diameter significantly less than said opening.

7. A self-contained fluid evacuator comprising:
  a. a container having at least one resilient wall capable of being deformed inwardly by applying an external pressure thereon, said resilient wall having sufficient resilience to return to an undeformed state upon release of said external pressure;
  b. a resilient inflatable member within said container, the interior surface of said container and the exterior surface of said inflatable member defining a fluid-receiving chamber therebetween, said inflatable member having an opening therethrough connecting the interior of said inflatable member with said exterior of said container, said opening including means for restricting flow through said opening from said inflatable member;

c. an inlet in said container in flow communication with said chamber, said inlet being adapted to receive said fluid;

d. an outlet in said container in flow communication with said chamber, said outlet including a one-way valve preventing flow into said chamber; and said opening being in flow communication with the atmosphere and said flow restricting means comprising a one-way valve preventing flow from said inflatable member, said inflatable member including means to vent the interior of said member to the atmosphere to deflate said member and generate negative pressure within said chamber.

8. The fluid evacuator of claim 7 wherein said venting means comprises a passage bypassing said flow restricting means, said passage including a manually controlled vent valve.

9. The fluid evacuator of claim 8 wherein said vent valve comprises a petcock valve.

10. The fluid evacuator of claim 7 wherein said venting means comprise a manual means for allowing flow through said one-way valve from said inflatable member.

11. A self-contained fluid evacuator comprising:

a. a container having at least one resilient wall capable of being deformed inwardly by applying an external pressure thereon; said resilient wall having sufficient resilience to return to an undeformed state upon release of said external pressure;

b. a resilient inflatable member within said container, the interior surface of said container and the exterior surface of said inflatable member defining a fluid-receiving chamber therebetween, said inflatable member having an opening therethrough connecting the interior of said inflatable member with the exterior of said container, said opening including means for restricting flow through said opening from said inflatable member;

c. an inlet in said container in flow communication with said chamber, said inlet being adapted to receive said fluid;

d. an outlet in said container in flow communication with said chamber, and a one-way valve only allowing flow into said chamber.

e. a common conduit for said inlet and said outlet, said common conduit comprising the sole means of flow communication to said chamber.

12. The fluid evacuator of claim 11 wherein said common conduit is Y-shaped and said inlet and said outlet are located in the separate branches of said Y, said inlet including a one-way valve preventing flow through said inlet from said chamber.

13. A self-contained fluid evacuator comprising:

a. a container having at least one resilient wall capable of being deformed inwardly by applying an external pressure thereon, said resilient wall having sufficient resilience to return to an undeformed state upon release of said external pressure;

b. a resilient inflatable member within said container, the interior surface of said container and the exterior surface of said inflatable member defining a fluid-receiving chamber therebetween, said inflatable member having an opening therethrough connecting the interior of said inflatable member with the exterior of said container, said opening including means for restricting flow through said opening from said inflatable member;

c. an inlet in said container in flow communication with said chamber, said inlet being adapted to receive said fluid;

d. an outlet in said container in flow communication with said chamber, said outlet including a one-way valve preventing flow into said chamber, said container having an uncollapsed shape wherein said container includes a bottom wall, first and second spaced opposing sidewalls, third and fourth sidewalls being spaced apart a distance greater than the spacing between said first and second sidewalls.

14. The fluid evacuator of claim 13 wherein said first and second sidewalls have a transverse outward curvature and said third and fourth sidewalls have a radius of transverse curvature which conforms to the shape of the natural, unimpeded shape of the adjacent portion of said resilient inflatable member during inflation of said inflatable member effecting substantially constant negative pressure at said inlet during deflation of said resilient inflatable member.

15. The fluid evacuator of claim 14 where said first and second sidewalls are substantially flat.

16. The fluid evacuator of claim 13 where the radius of transverse curvature of said third and fourth walls is half the distance between said first and second sidewalls.

17. The fluid evacuator of claim 16 where said bottom wall has a flat portion thereon to facilitate standing said container on a flat surface.

18. A self-contained fluid evacuator comprising:

a. a container having at least one resilient wall capable of being deformed inwardly by applying an external pressure thereon, said resilient wall having sufficient resilience to return to an undeformed state upon release of said external pressure;

b. a resilient inflatable member within said container, the interior surface of said container and the exterior surface of said inflatable member defining a fluid-receiving chamber therebetween, said inflatable member having an opening therethrough connecting the interior of said inflatable member with the exterior of said container, said opening including means for restricting flow through said opening from said inflatable member;

c. an inlet in said container in flow communication with said chamber;

d. a flexible tube having one extremity affixed to said inlet with said tube supplying said fluid to said inlet;

e. means for preventing flow through said inlet during inflation of said inflatable member;

f. an outlet in said container in flow communication with said chamber, said outlet including a one-way valve preventing flow into said chamber;

whereby closure of said inlet, deformation of said resilient wall inwardly and subsequent return of said resilient wall to its undeformed state lowers the pressure in said chamber whereby inflating said inflatable member by the flow of air through said opening into said inflatable member whereafter the deflation of said inflatable member produces a substantially constant negative pressure in said chamber thereby drawing fluid through said inlet when said inlet is open.

* * * * *

UNITED STATES PATENT AND TRADEMARK OFFICE
CERTIFICATE OF CORRECTION

PATENT NO. : 4,022,209
DATED : May 10, 1977
INVENTOR(S) : John R. Nehring

It is certified that error appears in the above-identified patent and that said Letters Patent are hereby corrected as shown below:

Column 10, claim 2, line 14, change "cloasing" to --closing--.

Column 12, claim 18, line 51, change "throughsaid" to --through said--.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks